(12) United States Patent
Bryan et al.

(10) Patent No.: US 9,821,006 B2
(45) Date of Patent: Nov. 21, 2017

(54) METHOD OF PRODUCING PHYSIOLOGICAL AND THERAPEUTIC LEVELS OF NITRIC OXIDE THROUGH AN ORAL DELIVERY SYSTEM

(71) Applicants: BOARD OF REGENTS OF THE UNIVERSITY OF TEXAS SYSTEM, Austin, TX (US); NEOGENIS LABS, INC., Austin, TX (US)

(72) Inventors: Nathan S. Bryan, Rockdale, TX (US); Jose G. Rocca, Doral, FL (US)

(73) Assignees: Board of Regents of the University of Texas System, Austin, TX (US); Neogenis Labs, Inc., Austin, TX (US)

(*) Notice: Subject to any disclaimer, the term of this patent is extended or adjusted under 35 U.S.C. 154(b) by 0 days.

(21) Appl. No.: 14/989,714

(22) Filed: Jan. 6, 2016

(65) Prior Publication Data

US 2016/0287628 A1    Oct. 6, 2016

Related U.S. Application Data

(63) Continuation of application No. 13/588,211, filed on Aug. 17, 2012, now Pat. No. 9,241,999, and a
(Continued)

(51) Int. Cl.
    *A61K 33/00*    (2006.01)
    *A61K 45/06*    (2006.01)
    (Continued)

(52) U.S. Cl.
    CPC .......... *A61K 33/00* (2013.01); *A61K 9/0053* (2013.01); *A61K 9/0056* (2013.01); *A61K 9/20* (2013.01); *A61K 9/2009* (2013.01); *A61K 9/2013* (2013.01); *A61K 31/195* (2013.01); *A61K 31/198* (2013.01); *A61K 31/375* (2013.01); *A61K 31/714* (2013.01); *A61K 36/21* (2013.01);
    (Continued)

(58) Field of Classification Search
    None
    See application file for complete search history.

(56) References Cited

U.S. PATENT DOCUMENTS

| 5,427,801 A | 6/1995 | Uehara |
| 5,922,610 A | 7/1999 | Alving et al. |

(Continued)

FOREIGN PATENT DOCUMENTS

| WO | 2008105730 A1 | 9/2008 |
| WO | 2009155689 A1 | 12/2009 |

(Continued)

OTHER PUBLICATIONS

Chung et al. (JBC. 1956,218:627-632).*

(Continued)

*Primary Examiner* — Ernst V Arnold
(74) *Attorney, Agent, or Firm* — Norton Rose Fulbright US LLP

(57) ABSTRACT

A composition and method of providing nitric oxide and nitrite therapy to patients whereby a therapeutic amount is bioavailable within approximately 30 minutes of administration. In embodiments of the invention, nitric oxide is produced in the oral cavity.

4 Claims, 9 Drawing Sheets

Related U.S. Application Data continuation-in-part of application No. 12/484,364, filed on Jun. 15, 2009, now Pat. No. 8,298,589.

(60) Provisional application No. 61/524,539, filed on Aug. 17, 2011.

(51) Int. Cl.

| | | |
|---|---|---|
| *A61K 31/195* | (2006.01) | |
| *A61K 31/375* | (2006.01) | |
| *A61K 9/00* | (2006.01) | |
| *A61K 9/20* | (2006.01) | |
| *A61K 31/198* | (2006.01) | |
| *A61K 31/714* | (2006.01) | |
| *A61K 36/21* | (2006.01) | |
| *A61K 36/734* | (2006.01) | |
| *A61K 38/44* | (2006.01) | |

(52) U.S. Cl.
CPC ............ *A61K 36/734* (2013.01); *A61K 38/44* (2013.01); *A61K 45/06* (2013.01); *C12Y 107/02001* (2013.01)

(56) References Cited

U.S. PATENT DOCUMENTS

| | | | | |
|---|---|---|---|---|
| 6,153,218 | A | * | 11/2000 | Barnwell ............ A61K 9/4808 424/451 |
| 6,709,681 | B2 | | 3/2004 | Benjamin et al. |
| 8,114,442 | B2 | * | 2/2012 | Tucker ................. A61K 9/0014 424/443 |
| 2001/0047035 | A1 | | 11/2001 | Boykin |
| 2002/0136750 | A1 | | 9/2002 | Benjamin et al. |
| 2004/0265360 | A1 | * | 12/2004 | Venturi .................. A23L 33/40 424/439 |
| 2005/0036949 | A1 | | 2/2005 | Tucker et al. |
| 2005/0037093 | A1 | | 2/2005 | Benjamin |
| 2005/0226906 | A1 | | 10/2005 | Moneymaker et al. |
| 2005/0226907 | A1 | * | 10/2005 | Moneymaker ......... A61K 31/00 424/439 |
| 2007/0014829 | A1 | | 1/2007 | Batchelor et al. |
| 2008/0207713 | A1 | | 8/2008 | Wang et al. |
| 2008/0226751 | A1 | | 9/2008 | Tucker et al. |
| 2008/0275093 | A1 | | 11/2008 | Garvey et al. |
| 2011/0086069 | A1 | | 4/2011 | Kevil et al. |
| 2011/0097316 | A1 | | 4/2011 | Hernuss |

FOREIGN PATENT DOCUMENTS

| | | |
|---|---|---|
| WO | 2010141719 A2 | 12/2010 |
| WO | 2010144817 A1 | 12/2010 |
| WO | 2010151505 A1 | 12/2010 |

OTHER PUBLICATIONS

Croitoru, M.D. (Journal of Chromatography B, 2012;911:154-161).*
Bjarnadottir, A. (Beetroot 101: Nutrition Facts and Health Benefits [online] retrieved on Feb. 14, 2017 from: https://authoritynutrition.com/foods/beetroot/; 8 pages).*
Webb et al. (Hypertension 2008; (51):784-790).*
Hord et al. (Am J Clin Nutr 2009;90:1-10).*
Alikulov et al., Biol. Bull. Acad. Sci. USSR 7(5):379-384 (Sep.-Oct. 1980) (abstract).
Becker et al., Z. Kardiol. 89(9):IX/88-IX/91 (2000).
Bjorne et al., J. Clin. Invest. 113(1):106-114 (Jan. 2004).
Bolli, J. Mol. Cell Cardiol. 33(11):1897-1918 (2001).
Brown et al., Eur. J. Pharmacol. 223(1):103-104 (1992).
Brown et al., FEBS Letters 356:295-298 (1994).
Bryan et al., Proc. Natl. Acad. Sci. USA 104(48):19144-19149 (Nov. 27, 2007).
Bryan, Free Radic. Biol. Med. 41(5):691-701 (2006).
Bryan et al., Nat. Chem. Biol. 1(5):290-297 (Oct. 2005).
Bryan et al., Proc. Natl. Acad. Sci. USA 101(12):4308-4313 (Mar. 23, 2004).
Carlstrom et al. (PNAS 2010, 107(41):17716-17720).
Castello et al., Cell Metab. 3(4):277-287 (Apr. 2006).
Chen et al., J. Am. Med. Assoc. 149(2):113-119 (May-Aug. 1952).
Chrominski, Mikolaj, et al., Protoporphyrin IX/Cobyrinate Derived Hybrids—Novel Activators of Soluble Guanylyl Clylase; National Instutues of Health, European J Org Chem. Mar. 1, 2013; 2013(8): 1530-1537.
Cormio et al. (Urology 2011, 77:119-122).
Cosby et al., Nature Medicine 9(12):1498-1505 (Dec. 2003).
Dejam et al., Blood Cells Mol. Dis. 32(3):423-429 (2004).
Dezfulian et al., Cardiovascular Res. 75(2):327-338 (2007).
Duncan et al., Nat. Med. 1(6):546-551 (Jun. 1995).
Duranski et al., J. Clin. Invest. 115(5):1232-1240 (May 2005).
Dykhuizen et al., Antimicrob. Agents Chemother. 40(6):1422-1425 (Jun. 1996).
Elrod et al., Arterioscler. Thromb. Vasc. Biol. 26(7):1517-1523 (2006).
Furchgott et al., J. Pharcol. Exp. Ther. 108(2):129-143 (1953).
Gladwin et al., Nat. Chem. Biol. 1(6):308-314 (Nov. 2005).
Goaz et al., J. Dent. Res. 40:355-365 (1961).
Grube et al., The Biology of Nitric Oxide, Enzymology, Biochemistry, and Immunology 4:201-204 (1994).
Hardwick et al., Clin. Sci. (Lond.) 100(4):395-400 (2001).
Hataishi et al., Am. J. Physiol. Heart Circ. Physiol. 291(1):H379-H384 (2006).
Herman et al., Eur. Heart J. 26(19):1945-1955 (2005).
Hunter et al., Nat. Med. 10(10):1122-1127 (Oct. 2004).
Ignarro, J. Physiol. Pharmacol. 53(4, Pt. 1):503-514 (2002).
Ignarro et al., Proc. Natl. Acad. Sci. USA 84(24):9265-9269 (Dec. 1987).
Jones et al., Am. J. Physiol. Heart Circ. Physiol. 276(5, Pt. 2):H1567-H1573 (1999).
Ishiwata et al., J. Food Hyg. Soc. Jpn. 16(2):89-92 (Apr. 1975).
Jones et al., Am. J. Physiol. Heart Circ. Physiol. 286(1):H276-H282 (2004).
Kelm, Biochim. Biophys. Acta 1411:273-289 (1999).
Kelm et al., Methods in Nitric Oxide Research, M. Feelisch and J.S. Stamler, Eds., Chichester, John Wiley and Sons, pp. 47-58 (1996).
Kelm et al., The Biology of Nitric Oxide, Physiological and Clinical Aspects, S. Moncada, M.A. Marietta, J.B. Hibbs, Jr. and E.A. Higgs, Eds., London, Portland Press 1:319-322 (1992).
Kim-Shapiro et al., Journal of Inorganic Biochemistry 99:237-246 (2005).
Kleinbongard et al., Free Radic. Biol. Med. 40(2):295-302 (2006).
Kleinbongard et al., Free Radic. Biol. Med. 35(7):790-796 (2003).
Kozlov et al., Shock 15(5):366-371 (2001).
Kozlov et al., FEBS Lett. 454(1-2):127-130 (1999).
Lauer et al., Proc. Natl. Acad. Sci. USA 98(22): 12814-12819 (Oct. 23, 2001).
Li et al., J. Biol. Chem. 279(17):16939-16946 (Apr. 23, 2004).
Li et al., J. Biol. Chem. 274(24):17325-17333 (Jun. 11, 1999).
Lundberg et al., Arterioscler. Thromb. Vasc. Biol. 25(5):915-922 (2005).
Ma et al., Circ. Res. 72(2):403-412 (1993).
Material Safety DataSheet. Sodium nitrite Msd S; pp. 1.6; Oct. 10, 2005; Scirenceltilleorn.
McKnight et al., Gut 40(2):211-214 (1997).
Meah et al., Food Addit. Contam. 11(4):519-532 (1994).
Moncada et al., Pharmacol. Rev. 43(2):109-142 (1991).
National Toxicology Program (NTP TR 495) (part of the National Institutes of Health (NIH), a component of the U.S. Department of Health and Human Services); "NTP Technical Report on the Toxicology and Carcinogenesis Studies of Sodium Nitrite (CasNo. 7632-00.0) in F344/N Rats and B6C3F.sub.1Mice (Drinking Water Studies)"; May 2001: pp. 1-274; NIH Publ. No. 01-3954; Research Triangle Park, NC.
Nohl et al., Bioorg. Chem. 29(1):1-13 (2001).
Nohl et al., Acta Biochim. Pol. 47(4):913-921 (2000).
Pabla et al., Circ. Res. 78(1):65-72 (1996).

(56) References Cited

OTHER PUBLICATIONS

Pique et al., Eur. J Pharmacol. 174(2-3):293-296 (1989).
Pluta et al., JAMA 293(12):1477-1484 (Mar. 2005).
Pronisias, Keith, et al., Vitamin B12 Derivatives as Activators of Soluble Guanylyl Clyclase; National Insitutes of Health, J Med Chem, Oct. 25, 2012; 55(20); 8943-8947.
Reichert et al., Am. J. Med. Sci. 159:158-180 (1880).
Reutov et al., Biochemistry (Mosc.) 63(7):874-884 (1998).
Rhodes et al., Biochem. Biophys. Res. Commun. 209(2):590-596 (Apr. 17, 1995).
Shah et al. (J Anal Bioanal Tech. 2013; S12:7 pages).
Sharina, Iraida, et al., Cobinamides are Novel Coactivators of Nitric Oxide Receptor that Target Soluble Guanylyl Cclase Catalytic Domain; Department of Internal Medicine, Journ of Pharmacology and Experimental Theraeputics; Dec. 12, 2011; vol. 340, No. 3; 723-732.
Sharma et al. (Biochemistry 2003, 42:8900-8908).
Sharp et al., Am. J. Physiol. Heart Circ. Physiol. 282(6):H2422-H2426 (2002).
Shiva (Redox Biology 2013(1 ):40-44).
Siegfried et al., Am. J. Physiol. 263(3, Pt. 2):H771-H777 (1992).
Spiegelhalder et al., Food Cosmet. Toxicol. 14:545-548 (1976).
Takehara et al., Cell Struct. Funct. 21(4):251-258 (1996).
Tannenbaum et al., J. Natl. Cancer Inst. 53(1):79-84 (Jul. 1974).
Tannenbaum, Science 205(4413):1333-1335 (Sep. 1979).
Tischner et al., FEBS Lett. 576:151-155 (2004).
Tsuchiya et al., Am. J. Physiol. Heart Circ. Physiol. 288(5):H2163-H2170 (2005).
Vallance, Gut 40(2):288 (1997).
van Maanen et al., Cancer Detect. Prev. 20(6):590-596 (1996).
Walker et al., Biochem. Soc. Trans. 24(3):423S (1996).
Walters et al., Biochim. Biophys. Acta 143(2):310-318 (1967).
Webb et al., Proc. Natl. Acad. Sci. USA 101(37):13683-13688 (Sep. 14, 2004).
Yoshida et al., Int. Arch. Occup. Environ. Health 52:103-115 (1983).
Zand, et. al.; "All-Natural Nitrite and Nitrate Containing Dietary Supplement Promotes Nitric Oxide Production and Reduces Triglycerides in Humans"; Apr. 2011, Nutrition Research, vol. 31, pp. 262-269.
Zweier et al., Nat. Med. 1(8):804-809 (Aug. 1995).

* cited by examiner

METHOD OF PRODUCING PHYSIOLOGICAL AND THERAPEUTIC LEVELS OF NITRIC OXIDE THROUGH AN ORAL DELIVERY SYSTEM

PRIORITY

This application claims priority to U.S. Provisional Patent Application 61/524,539, filed Aug. 17, 2011, and this application is a continuation-in-part of U.S. patent application Ser. No. 12/484,364, filed Jun. 15, 2009, both of which applications are hereby incorporated by reference herein in their entirety.

BACKGROUND

Nitric Oxide Production Issues

Many diseases are characterized by or associated with insufficient nitric oxide production. Experimental and clinical studies demonstrate that insufficient nitric oxide production is associated with major cardiovascular risk factors, such as hyperlipidemia, diabetes, hypertension, smoking and atherosclerosis. Nitric oxide production is also a predictive indicator of future atherosclerotic disease progression. Unfortunately, the ability to generate nitric oxide decreases with age resulting in increased risk of heart and vascular disease.

The dysfunctional nitric oxide synthase (NOS) nitric oxide pathway is considered an early marker for various cardiovascular disorders. Decreased bioavailability of endothelial nitric oxide plays a crucial role in the development and progression of a number of human diseases. Endothelial dysfunction results from decreased nitric oxide production or increased degradation of nitric oxide. In certain aspects endothelial dysfunction can be defined as the inability to generate NO. Endothelial dysfunction is a physiological dysfunction of normal biochemical processes carried out by the endothelium, the cells that line the inner surface of all blood vessels including arteries and veins (as well as the innermost lining of the heart and lymphatics). Endothelial dysfunction is associated with several cardiovascular disorders, including atherosclerosis.

Prior attempts to restore nitric oxide homeostasis have met significant challenges. L-arginine and antioxidant supplements have consistently failed in clinical trials. It is known that NOS enzymes produce nitric oxide by catalyzing a five electron oxidation of the guanidino nitrogen of L-arginine. While nitric oxide is produced through oxidation of the semi-essential amino acid L-arginine by NOS, the L-arginine-nitric oxide pathway is dysfunctional in patients with endothelial dysfunction. Thus, feeding the nitric oxide pathway through L-arginine supplementation is potentially both ineffective and detrimental through the production of superoxide instead of nitric oxide.

Prior attempts to enhance nitric oxide production with organic nitrates such as nitroglycerin have faced challenges. Early entry therapy with organic nitrates do not significantly improve survival in myocardial infarction but increases the beneficial effects of the Angiotensin Converting Enzyme (ACE)-inhibitor enalapril by 50%. Certain short-term experimental and clinical investigations suggest that nitrate tolerance induced by nitroglycerin is associated with toxic effects in the vasculature. Chronic and long-term organic nitrate therapy has been associated with reduced survival when used in patients with coronary artery disease. Endothelial dysfunction induced by a continuous treatment with nitroglycerin may be an additional risk for patients who receive continuous nitroglycerin to treat conditions such as unstable angina and acute heart failure.

Attempts targeting delivery of nitric oxide to precise cellular locations have also faced challenges. The most widely known and effective means for targeted delivery to the pulmonary circulation is inhaled nitric oxide, which requires specialized inhaling equipment. Biomaterials for sustained release of nitric oxide for topical applications for wound healing, infections, etc. are still in development. Nanoparticle delivery of nitric oxide is still emerging, particularly in cancer biology. NO-eluting stents or nitric oxide-coating of orthopedic implants for preventing biofilm growth and infection is also still in development. Phosphodiesterase inhibitors, such as sildenafil, do not directly affect nitric oxide production but act through affecting the downstream second messenger of nitric oxide, cyclic guanosine monophosphate (cGMP).

Oral Formulation Concerns

An oral disintegrating tablet (ODT) is a solid oral dosage form that disintegrates and dissolves in the mouth without water within 1 minute or less. A similar term used is Orodisperse, which refers to a tablet that can be placed in the mouth where it disperses rapidly before swallowing. These tablets are differentiated from regular conventional compressed or molded sublingual tablets and chewable tablets that require more than a minute to dissolve in the mouth. In the literature, ODTs also are identified as rapidly-dissolving tablets, orally disintegrating, quick-dissolve, orodisperse, mouth-dissolving, fast-melt, and rapid-disintegrating tablets.

ODTs were designed for children and the elderly or for any individual that has difficulty with swallowing, especially entire tablets or capsules, commonly referred as dysphagia. With an ODT tablet, all of the components will liquefy in the mouth and then the individual swallows the liquid. However, there are a number of disadvantages and complexities associated with the formulation development and scale-up process of ODTs, including drug loading, taste masking, friability, high facility and manufacturing costs, and stability of the finished product.

Furthermore, taste masking creates numerous challenges for ODTs. Because the active and inactive components of the formula dissolves in the mouth, any taste of any poor tasting component must be covered, either by a flavoring technique or by a coating system such as microencapsulation. The product could also be granulated with slow-dissolving components, but in some embodiments the resulting particle should not be gritty such that it results in a small enough particle size to be unable to feel it in the mouth.

Poor friability is the most frequent problem found in ODTs. For a compressible tablet to dissolve instantly, it may be quite friable. However, making the tablet harder and less friable may negatively impact the fast disintegration and dissolution time. Generally, an ideal ODT must have a balance between durability, friability and speed of disintegration/dis solution.

Embodiments Satisfy an Unmet Need

Accordingly, there exists a large unmet need to recapitulate nitric oxide homestatis in the body using an effective delivery system. Oral disintegrating tablets were previously considered unsuitable because they dissolve in the mouth, where oral dispersion of nitric oxide was perceived as ineffective. Oral disintegrating tablets are designed for children, the elderly and individuals with difficulty swallowing. Complexities challenge the formulation, development and scale-up process of oral disintegrating tablets, including drug loading, taste masking, friability, high facility and manufacturing costs, and stability of the finished product.

Regular tablets and capsule do not allow the proper reaction to take place and minimize nitric oxide generation. Capsules pass through the gastrointestinal tract and release their contents in the stomach. However, many people taking proton pump inhibitors or who may have achlorhydria for other reasons may not experience the same benefit since low pH in the stomach is required to generate NO from nitrite. Nitrosative chemistry occurring in the stomach also has the potential to form potentially carcinogenic N-nitrosamines. By slowly titrating the saliva one can avoid the burst of nitrosative chemistry that would occur at once in the stomach.

Embodiments of the present invention have thus emerged to restore nitric oxide homeostasis in an endothelium-independent manner through a safe and effective oral delivery system. Embodiments of the present invention restore physiological levels of nitric oxide in the body thereby treating or preventing disease. Embodiments of the present invention overcome challenges faced in the prior art by delivering bioactive nitric oxide sources to targeted locations, including the mouth where such sources may be reacted to produce nitric oxide which is absorbed in the mouth and then circulated in the body. The delivery system includes an ideal balance of durability, friability and speed of disintegration/dissolution oral dose which have broad applications and utility in health.

BRIEF SUMMARY

In embodiments of the invention, there are methods and compositions for treating an individual in need of producing sufficient levels of nitric oxide (NO). Embodiments of the invention encompass a particular oral delivery system that allows production of physiological and therapeutic levels of NO in an individual in need thereof.

In embodiments of the present invention, a novel solid oral dosage form is utilized to overcome deficiencies in the art for NO therapy and to overcome many of the formulation disadvantages previously presented. A stable, robust, process-friendly, good-tasting (in at least some cases) oral tablet has been formulated that disintegrates rapidly in the mouth. This tablet facilitates the controlled release of the active components of embodiments of the invention to generate nitric-oxide in situ by liquefying the contents in the oral/buccal cavity. This technology is useful as a means to treat, prevent or cure conditions associated with nitric oxide insufficiency. The embodiment can be formulated using fast melt technology as a dissolvable lozenge (for example) that becomes activated and generates NO upon dissolution.

The delivery system makes use of the nitrogen cycle, which enables dietary sources of nitrate to be serially reduced to nitrite and nitric oxide. In one embodiment the delivery system includes nitric oxide-producing components formed from natural sources of both nitrite and nitrate, which dissolve slowly in in-vivo. The dissolution of the delivery system over a short period, such as on the order of minutes, for example, 5-6 minutes, allows for bacteria existing in vivo to metabolize nitrite and/or nitrate molecules to produce nitric oxide in vivo. Nitric oxide-producing components formed from potent sources of bioactive nitric oxide, such as beetroot juice, in low physiological amounts of nitrite avoid potential toxicity. Reductase is another nitric oxide-producing components. Reductase activity is preferably included for effective metabolism of nitrate and nitrite to NO rather than promoting nitrosative chemistry. The delivery system thus need not rely 100% on in vivo bacteria, overcoming the variability of relevant bacteria in the population. The reductase may be from one or more botanicals having an oxygen independent nitrite reductase. The nitrite, nitrate and/or reductase or other components that produce nitric oxide remain inert until they are dissolved in vivo where they are activated.

One embodiment of the present invention provides NO generation in the first 30 minutes of dosage in order to maximize therapeutic effect. The maximization is due to absorption kinetics, site of delivery, and combinations thereof. A regular tablet/capsule will have not allowed the proper reaction to take place and will minimize NO generation. The gastrointestinal (GI) tract is a heterogeneous system, and regular ingestible dosage forms will have to start releasing its contents in the stomach at a relatively low pH. A sustained release preparation will not be effective for the reaction of the components to take place and will minimize absorption due to variability in pH, transit time and degradation kinetics.

The delivery system is preferably administered orally in the buccal cavity. The preferred delivery system includes a controlled release of the active components to generate nitric-oxide in situ by liquefying the delivery system in the upper part of the GI tract. Components may include natural sources of nitrites and nitrates such as berries, herbals and botanicals. Oral delivery of the anions in the buccal cavity overcomes any issues with uptake in the gut. Slowly titrating with saliva avoids the nitrosative chemistry burst that would otherwise occur at once in the stomach. The delivery system may make use of the existing bacteria in the oral cavity, such as bacteria existing in the crypts of the tongue. Including such natural product chemistry in the delivery system overcomes the 0.01% reduction efficacy in normal blood and tissue and increases to greater than 90% reduction efficacy in the buccal cavity and circulation. Delivery in the buccal cavity enables the delivery system to generate nitric oxide without acid residing in the stomach. Thus, embodiments of the invention satisfy a need for a delivery system that will allow the reaction in situ and in the upper part of the GI tract, preferably in the buccal cavity, so that nitric oxide deactivation can be minimized. The slow release of NO from formulations of embodiments of the present invention leads to longer half-life of nitrite in the plasma that otherwise would not happen in a pill or capsule activated in the stomach.

In embodiments of the invention, the formulation allows the gradually controlled dissolution of the lozenge and activation by the saliva that releases free nitric oxide in the mouth that is then absorbed and transported throughout the body. In embodiments of the invention, the formulation (such as a lozenge) is completely inert until activated by saliva.

Because at least some components in embodiments of the invention are reactive with each other, this presented incompatibilities in the dosage form; therefore, a low moisture content formula was employed. One embodiment includes an overall moisture content of less than 5% and at least in some cases less than 3%; otherwise, the formulation will completely de-activate and will turn into a black compact, for example. Further, in embodiments wherein sodium nitrite and hawthorn are employed, for example, these components can be problematic in that if they are in direct contact they will cause color change and nitrate depletion. Embodiments of one formula prevent such an event from happening because of the dilution with the other components/fillers and/or because of the low moisture content. In one embodiment a sufficient amount of inert components are provided to prevent the reactive components (nitrite, nitrate, reductase) from coming in contact. Other embodiments of the invention address the difficulty whereby a formula is needed with a relatively low water content. The delivery system is preferably formulated with a relatively low water content so that components do not react. To prevent reaction between reactive components, a low moisture formula in which the overall moisture content is less than 5% and preferably less than 3% is contemplated. High moisture may prematurely activate the delivery system and turn it into a black compact in certain embodiments. The delivery system is preferably packaged to resist moisture. A unit dose blister with minimal water permeation film is preferred. The delivery system may be coated or directly compressible (DC) grade ascorbic acid to minimize surface area exposure and reaction.

In embodiments of the invention, the formulation is protected by using packaging preservation, such as a unit dose blister with minimal water permeation film. Otherwise, the formulation will start decomposing. In some embodiments, the present invention uses a coated or DC grade ascorbic acid to minimize surface area exposure and reaction.

In certain embodiments the blend of components in the present invention makes a palatable and process-friendly tablet. Dealing with the frequent variability of natural components like berries/herbals/botanicals are rather difficult to process into uniform and durable tablets, because compression is frequently poor and cohesive.

Certain components of the delivery system may react with each other. The components remain inert until delivery. Nitrosation inhibitors to prevent nitrosative chemistry and components that minimize nitric oxide formation until delivery may be included; such components may include Vitamin C, polyphenols, organic chemicals (natural and/or synthetic) characterized by the presence of large multiple phenols units; they are beneficial to health because of their antioxidant activity), and other antioxidants. The delivery system may also suspend the reactive components from coming into reactive contact with each other so they to remain inert in the dosage form. Sodium nitrite and hawthorn are reactive, for example. In one embodiment, the delivery system positions these components from coming into contact with each other. Proper dilution to provide a physical-chemical separation also prevents the components from reacting prior to delivery. In one embodiment, the delivery system is granulated and a sufficient amount of non-reactive granules are included so as to mitigate surface contact of reactive granules.

The delivery system includes a consistent source of bioactive nitric oxide to mitigate variability or conditions that may exist across a large population including absorption issues, oral bacteria variability, stomach acid production and endothelial dysfunction.

The delivery system may also include flavoring or incorporate a flavor masking coating system, such as microencapsulation. The components are preferably granulated and slow dissolving, but upon dissolution the resulting particles are preferably not be gritty so as to result in small particles being felt in the mouth. The delivery system may be compressed into a stable and durable form. In certain embodiments, the formulation lacks any adhesives.

In some embodiments, the delivery system includes a fluid that does not cause the nitric oxide generating components to react, such as by formulating the fluid with a pH level that does not react with nitrites or nitrates. The fluid preferably includes a pH different than the necessary pH level for reducing nitrite or nitrates to nitric oxide. In one embodiment, the pH of the fluid is higher than the pKa of the nitrite or nitrate. In another embodiment, there may be a liquid delivery system whereby multiple liquid compartments may be separated until placed in the mouth.

The delivery system may be in the form of a lozenge, strip, food, powder, liquid, fluid, gel, emulsion, ointment, oral disintegrating tablet, oral disintegrating powder, sublingual tablet or strip, oral dispersible powder, and the like, or any other form known to a person of skill in the art for maintaining nitric oxide generating components in an inert state until they are introduced in-vivo.

In embodiments of the invention, the amount of nitric oxide generated is physiological in nature and is an amount normally produced by a healthy endothelium of a 70-80 kg person over a 24 hour period. The delivery system recapitulates physiological nitric oxide production by providing an immediate source of exogenous nitric oxide through reduction of nitrate and nitrite and by promoting endogenous nitric oxide production by the endothelium by supporting the biochemistry of this reaction. The result is a very safe and efficacious nitric oxide delivery system that can be harnessed for many uses including but not limited to exercise performance or any medical condition characterized by or associated with a nitric oxide deficiency. The delivery system also provides for dietary and/or therapeutic intervention to replete nitric oxide homeostasis.

In embodiments of the invention, there is a method of treating conditions of NO insufficiency in humans. Humans with conditions associated with NO insufficiency such as coronary artery disease, peripheral artery disease, diabetes, smokers, hypertension, sedentary lifestyle and/or family history of cardiovascular disease can be treated with formulations of embodiments of the invention, as an example. In specific embodiments, an individual in need thereof is administered one or more formulations of the invention. In specific cases, one or two lozenges (or other configuration) per day are used as a means to restore NO homeostasis.

In certain aspects of the invention, absorption is independent of one or more known physiological modifiers. That is, the formulation (such as an ODT) delivers NO independent of any of the limitations that people may have (including endothelial dysfunction, dysbiosis in the mouth, use of proton pump inhibitors, poor diet, etc.).

In embodiments of the invention, there is a composition comprising nitrite and an orally dispersable medium. The composition may further comprise a reductase to donate an electron to nitrite for generating nitric oxide when reacted with nitrite. In specific embodiments, the delivery system is comprised of a lozenge, liquid, powder, solid (dissolvable in oral cavity), semi-solid (cream, gel, emulsion, suspension) heterogenic liquid (multi-phase), film, topical, or suppository. In certain aspects, the orally dispersable medium includes one or more of a sugar, dispersing agent, flavor, sweetener, color, alcohol, maltodextren, or other filler (organic: cellulosis; inorganic: phosphate salt). In specific embodiments, the dispersable system includes a barrier for preventing contact of the nitrite and reductase (to minimize exposure of the surfaces). In some cases, the barrier is formed of a sugar, dispersing agent, flavors, sweetener, color, alcohols, maltodextren, or other fillers (organic: cellulosis; inorganic: phosphate salt) to provide separation between the nitrite and reductase. The delivery system is adapted to cause the nitrite and reductase to come in contact in situ and generate nitric oxide, in particular embodiments.

In some embodiments of the invention, there is a tripartite composition comprising nitrite, disintegrating agent, and compactable excipient. In certain embodiments, the three parts are integrated into a single form (a compact). In some cases, the disintegrating agent tends to absorb fluid upon contact with fluid e.g., like a sponge the agent facilitates retention of fluid to allow for volume expansion. In some cases, the disintegrating agent is inert and/or compressible. A compactable excipient is adapted to be compressed and maintain the compressed form. In some cases, a compactable excipient is chemically inert, does not tend to absorb fluid, is non-hydroscopic, protects water-sensitive actives; does not react with actives (i.e, nitrite, or disintegrating agent) and/or has a narrow particle size distribution. In some cases, the composition is compressible into a tablet, and the tablet may be of a form that maintains a compressed form after being compressed. In specific cases, the disintegrating agent causes the compactable excipient to break apart upon expansion.

In some embodiments, there is a composition comprising nitrite and a carrier for nitrite. The carrier provides for administration (i.e., delivery) of nitrite to a buccal cavity. In specific embodiments, the carrier does not react with the nitrite (i.e., is inert, both in package and during administration). The carrier does not impede the reaction of nitrite with other components, nor does it impede the absorption of nitrite in said buccal cavity, in particular embodiments, and the carrier does not tend to swell upon contact with a fluid (i.e., is non-hydroscopic), in particular embodiments. In specific cases, the carrier is adapted to maintain uniform distribution of nitrite in a package (and during administration). The carrier may be digestive (or non-digestive); the carrier may be organic (or inorganic). In specific embodiments, the nitrite is formed of a salt, from a plant, natural occurring product, and/or cultured vegetable extract. In particular cases, the carrier has less than or equal to 50% particle size difference from the nitrite. In specific embodiments, the carrier has a particle size ranging from 50 to 500 microns.

Composition embodiments of the invention may comprise reductase for nitrite; ascorbic acid; and polyphenols, and the compositions may further comprise a disintegrating agent and/or a compactable excipient. In some embodiments, there is a composition comprising nitrite; reductase for the nitrite; ascorbic acid; and/or polyphenols; a composition may also comprise a disintegrating agent; and a compactable excipient.

In some embodiments, there is a method of enhancing cardiovascular performance in an individual, comprising the step of administering a composition of embodiments of the invention to the individual. In specific embodiments, the composition includes an herb with a functional nitrite reductase activity, wherein the herb is hawthorne berry, schizandra, or bilberry, or any other nitrite reducing agent.

In therapeutic method embodiments, one can administer a dosage from about 0.01 mg/kg/day to about 15 mg/kg/day sodium nitrite, from about 1 mg/kg/day to about 50 mg/kg/day sodium nitrate, and from about 1 mg/kg/day to about 25 mg/kg/day ascorbic acid, for example. In specific embodiments, the composition further comprises L-arginine and/or L-citrulline. In some embodiments, administering is of a dosage from about 2 mg/kg/day to about 50 mg/kg/day l-arginine and/or L-citrulline. In some embodiments, there are components with nitrite reductase activity that are herbs, natural products, or combinations thereof. In specific embodiments, components with nitrite reductase activity are hawthorne berry, bilberry, or combinations thereof.

In some embodiments of the invention, there is a composition comprising at least one nitric oxide-producing component; and an orally dispersable system configured to produce nitric oxide in the oral cavity. In specific embodiments, the nitric oxide-producing component comprises nitrite, nitrate, nitrite reductase, or a combination thereof. In specific embodiments, the dispersable system is configured as a lozenge, liquid, powder, solid, semi-solid, cream, gel, emulsion, suspension, heterogenic liquid, film, or topical. In some cases, the composition comprises one or more of a sugar, dispersing agent, flavor, sweetener, color, alcohol, maltodextren, or filler. In particular embodiments, the dispersable system is configured to comprise a barrier for preventing contact of two or more species of the nitric oxide-producing component. In certain aspects, the two or more species are nitrite and nitrite reductase. The barrier may be formed of any suitable composition, but in specific embodiments the barrier is formed of a sugar, dispersing agent, flavors, sweetener, color, alcohol, maltodextren, or filler. The composition may further comprise a disintegrating agent, a compactible excipient, or both.

In embodiments of the invention, there is a delivery system comprising at least one nitric oxide-producing component; and a dispersable medium adapted to be consumed in the oral cavity; wherein the nitric oxide-producing component is adapted to generate nitric oxide in vivo upon consumption of the dispersable medium. In specific embodiments, the dispersable medium is dissolvable in the oral cavity. In specific embodiments, the dispersable medium is dissolvable in five minutes (or about five minutes) or less. In specific embodiments, the delivery system is adapted to generate nitric oxide in the oral cavity. In particular cases, the nitric oxide-producing component is adapted to generate nitric oxide in vivo in response to dissolution of the delivery system in the gastro intestinal tract. In certain aspects, the delivery system is formed of a lozenge, liquid, powder, solid, semi-solid, cream, gel, emulsion, suspension, heterogenic liquid, film, or topical. In certain embodiments, the dispersable medium comprises one or more of a sugar, dispersing agent, flavor, sweetener, color, alcohol, maltodextren, or filler. The nitric oxide-producing component is comprised of a nitrite, nitrate, or reductase or a combination of nitrite, nitrate and reductase, in particular aspects. In some cases, the system further comprises a barrier for preventing contact of two or more species of the nitric oxide-producing component, such as nitrite and nitrite reductase. The barrier may be formed of a sugar, dispersing agent, flavors, sweetener, color, alcohol, maltodextren, or filler, in certain aspects. The composition may further comprise a disintegrating agent, a compactible excipient, or both. In some cases, the disintegrating agent absorbs fluid upon contact with fluid. In certain aspects, the compactable excipient is adapted to maintain the delivery system in a compressed form. In some embodiments, the compactable excipient is chemically inert, does not absorb fluid, is non-hydroscopic, protects water-sensitive nitric oxide-producing components, does not react with nitric oxide-producing components and/or has a narrow particle size distribution. In certain cases, the disintegrating agent causes the compactable excipient to break apart upon expansion.

In some embodiments, there is a composition comprising a nitrite; reductase for said nitrite; and a carrier for administration of said nitrite and said reductase to the buccal cavity. In specific embodiments, the carrier is adapted to cause the nitrite to react with the reductase for said nitrite upon administration to the buccal cavity. In some cases, the carrier is adapted to maintain physical separation of the nitrite and the reductase for said nitrite prior to administration. In some cases, the composition is a lozenge liquid, powder, solid, semi-solid, cream, gel, emulsion, suspension, heterogenic liquid, film, or topical. In certain cases, the carrier is of an amount sufficient to prevent contact of said nitrite and said nitrite reductase in a package. In certain embodiments, the nitrite is formed of a salt, is from a plant, is from a natural product, and/or is from cultured vegetable extract. In some cases, the carrier has less than or equal to 50% particle size difference from nitrite. In specific embodiments, the carrier has a particle size ranging from 50 to 500 microns. In some embodiments, the composition further comprises ascorbic acid and/or at least one polyphenol.

In some embodiments, there is a method of increasing levels of nitric oxide in an individual, comprising the step of delivering a therapeutically effective amount of any composition of embodiments of the invention. In specific embodiments, the individual has endothelial dysfunction. In some embodiments, the individual has hyperlipidemia, diabetes, hypertension, atherosclerosis and/or is a smoker.

In some embodiments, there is a method of enhancing cardiovascular performance in an individual, comprising the step of administering a composition of embodiments of the invention to the individual.

The foregoing has outlined rather broadly the features and technical advantages of certain embodiments of the invention in order that the detailed description of the invention that follows may be better understood. Additional features and advantages of the inventions will be described hereinafter which form the subject of the claims of the inventions. It should be appreciated by those skilled in the art that the conception and specific embodiment disclosed may be readily utilized as a basis for modifying or designing other structures for carrying out the same purposes of the present inventions. It should also be realized by those skilled in the art that such equivalent constructions do not depart from the spirit and scope of the invention as set forth in the appended claims. The novel features which are believed to be characteristic of the inventions, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

In FIG. 4A the barrier formed of a greater concentration of inert particles than active particles. In FIG. 4B, the barrier is a physical layer of inert material that separates the active ingredients on the tablet.

DETAILED DESCRIPTION

Figure 1:
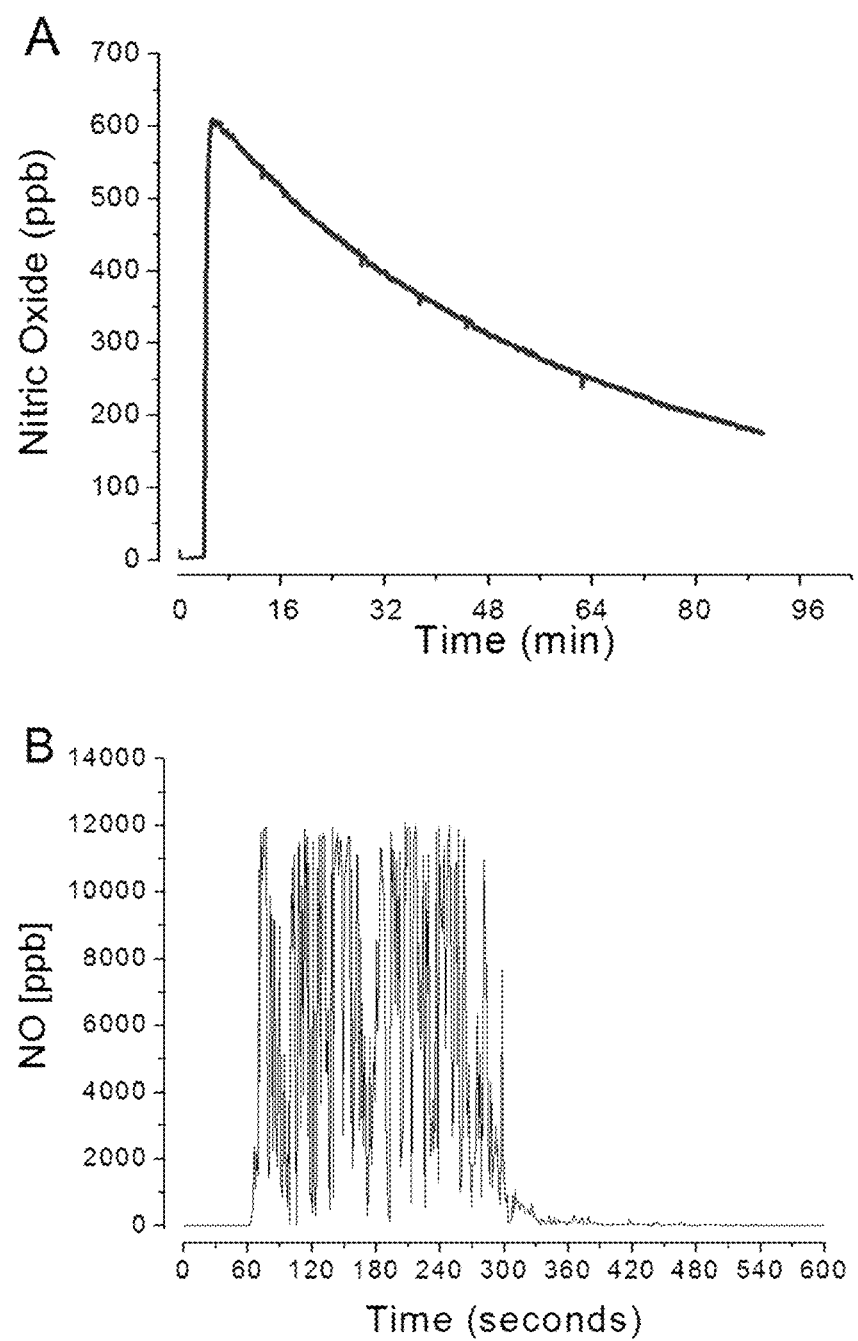
FIG. 1 (A) NO release profile of NO delivery system when dissolved in neutral buffer solution connected to a NO analyzer; (B) NO release profile when allowed to dissolve in the mouth of a human subject.

It is becoming increasingly clear that many diseases are characterized or associated with perturbations in nitric oxide (NO) production/signaling. Therapeutics or strategies designed to restore normal NO homeostasis will likely have broad application and utility in human health. The production of nitric oxide is one of the most important biological processes in the body. Despite NO's known and accepted importance in human physiology, there have been no hallmark therapeutic breakthroughs or effective strategies developed to enhance or restore NO homeostasis in humans at risk for cardiovascular disease. Developing such strategies or technologies to restore and replete NO availability, both through restoration of endothelial NO production and in an endothelium-independent manner, is of paramount importance and could potentially save millions of lives worldwide and lessen the burden on the health care system.

Providing a rich source of nitrate either through direct supplementation with nitrate salts or through nitrate rich foods such as beet root, for example, will increase circulating levels of nitrite. However, because of the inherent inefficiencies that exist for reducing nitrite to NO along the physiological oxygen gradient, this step in the pathway must be enhanced to effectively utilize nitrite to make NO. One could accomplish this by supplying more nitrate to generate supraphysiological concentrations of nitrite, or one could introduce a robust nitrite reductase to more effectively reduce nitrite to NO along the physiological oxygen gradient in vivo. The inventors have identified a number of exemplary herbs that can serve such a role. In some embodiments, this system uses physiological concentrations of nitrate and nitrite, supplied by the diet, to effectively generate NO through the step-wise reduction of nitrate and nitrite by supplying the necessary substrates and machinery to perform these steps.

There are specific and select communities of bacteria capable of reducing nitrate to nitrite. These bacteria are absent in varying amounts across the population. As much as 30-40% of the healthy population may not have the right oral microbiota in their saliva to reduce nitrate to nitrite, however. As a result, the population does not consistently experience the nitric oxide benefit of high nitrate sources, such as beet root juice, green leafy vegetables or other high nitrate sources.

Ineffective microbiota may be because of use of antiseptic mouthwash, antibiotics, or poor oral hygiene and overgrowth of pathogenic bacteria in the mouth that outcompete the communities of nitrate reducing bacteria. Iodine and other anions also compete with nitrate for binding and uptake in the duodenum. People taking iodine supplements may not effectively absorb nitrate in the gut and therefore reduce the amount that is concentrated in the saliva. Therefore, developing a system for overcoming this limitation in the population is novel and ensures product consistency and reduces person to person variability.

The human nitrogen cycle involves the formation of nitric oxide in the acid stomach from the acid disproportionation of nitrite. The pKa of nitrite is 3.4, meaning at pH 3.4, fifty percent of the nitrite forms nitric oxide. In the normal healthy stomach with a pH of less than 2, there is substantial nitric oxide formation from this pathway. However in populations with achlorhydria, nitric oxide formation is interrupted. This often occurs in patients taking proton pump inhibitors (PPI) or who have insufficient stomach acid production for other reasons. This represents a significant segment of the population, because PPI's are frequently prescribed medications throughout the developed world.

Blood and tissue nitrite reduction is grossly inefficient along the physiological oxygen gradient. Enzyme systems such as hemoglobin, myoglobin and xanthine oxidoreductase can reduce nitrite to nitric oxide, but this process is inhibited by oxygen. Blood and tissue research of experimental mammals reveal that nitrite to nitric oxide occurs at about 0.01% efficiency. One needs a high concentration of nitrite in the blood and tissues to generate any appreciable amount of bioactive nitric oxide. High concentrations of nitrite in blood can cause methemoglobinemia and therefore there is a delicate balance between risk and benefit.

There are certain botanical sources, natural foods and diets that confer nitric oxide activity. Nitrate in the diet (primarily from green leafy vegetables or beet root) is reabsorbed in the proximal intestines and concentrated in the salivary glands. Salivary glands extract nitrate from plasma and, as a result, levels of salivary nitrate are 10-20 fold higher than in plasma. Humans, unlike prokaryotes, are believed to lack the enzymatic machinery to reduce nitrate back to nitrite. However, due to the commensal bacteria that reside within the human body, these bacteria can reduce nitrate, thereby supplying an alternative source of nitrite and nitric oxide. Similar commensal bacteria exists in other animals, including mammals such as dogs, cats, horses, cattle, mice and rats.

The bioactivation of nitrate from dietary or endogenous sources requires its initial reduction to nitrite, and because mammals lack specific and effective nitrate reductase enzymes, this conversion is mainly carried out by commensal bacteria in the mouth and gastrointestinal tract and on body surfaces. These oral facultative anaerobic bacteria residing mainly in the crypts of the tongue, then reduce nitrate to nitrite by the action of nitrate reductase enzymes. These bacteria use nitrate as an alternative electron acceptor to gain cellular energy in the form of adenosine triphosphate (ATP) in the absence of oxygen. Approximately 25% of ingested nitrate is secreted in saliva, where some 20% (or approximately 5-8% of the nitrate intake) is converted to nitrite by commensal bacteria on the tongue. The salivary nitrate levels can approach 10 mM and nitrite levels 1-2 mM after a dietary nitrate load. When saliva enters the acidic stomach (1-1.5 L per day), much of the nitrite is rapidly protonated to form nitrous acid (pKa~3.3), which decomposes further to form nitric oxide and other nitrogen oxides. Once nitrite is absorbed and circulated, it is taken up by peripheral tissues and can be stored in cells. The one-electron nitrite reduction to nitric oxide can occur in a much simpler mechanism than the two-electron reduction of nitrate by bacteria. The 1-electron reduction of nitrite can occur by ferrous heme proteins (or any redox active metal) through the following reaction:

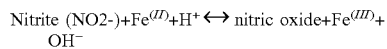

Nitrite (NO2-)+Fe$^{(II)}$+H$^+$ ↔ nitric oxide+Fe$^{(III)}$+OH$^-$

This is the same biologically active nitric oxide as that produced by NOS, with nitrite rather than L-arginine as the precursor and is a relatively inefficient process. This nitrate-nitric oxide pathway has been shown in both animals and humans to reduce blood pressure, restore endothelial function, protect from myocardial ischemia-reperfusion injury, prevent microvascular inflammation and reduce triglycerides and c-reactive protein. Therefore there exists a pathway for increasing nitric oxide bioavailability within the body through supplementing nitric oxide-rich or nitric oxide-active food components that contain adequate amounts of nitrate and/or nitrite and anti-oxidants to facilitate reduction to nitric oxide and to inhibit any unwanted nitrosation reactions.

Endogenous pathways for reducing nitrite to nitric oxide are inefficient and only occur under low or no oxygen concentrations. Much of the recent focus on nitrite physiology is because of its ability to be reduced to nitric oxide during ischemic or hypoxic events. Nitrite reductase activity in mammalian tissues is linked to the mitochondrial electron transport system, protonation, deoxyhemoglobin, and xanthine oxidase. Nitrite can also transiently form nitrosothiols (RSNOs) under both normoxic and hypoxic conditions. Steady state concentrations of tissue nitrite and nitroso are affected by changes in dietary nitric oxidex (nitrite and nitrate) intake.

From screening natural product libraries and many extracts from traditional medicines, there has been identified an oxygen-independent nitrite reductase that can effectively reduce nitrite to nitric oxide. Utilizing and harnessing the natural product chemistry along with the commensal bacteria in the mouth, the inventors have developed a unique and novel system for delivering nitric oxide as a means to restore nitric oxide homeostasis in humans. The formulation preferably comprises nitrite, nitrate and herbs with nitrite reductase activity, which provides a delivery system for generating nitric oxide in an endothelium-dependent and independent manner. The formula preferably includes a blend of nitric oxide active herbs that act to replete and restore nitric oxide production in the human body by exploiting the nitrate-nitrite-nitric oxide pathway.

The disclosed embodiments provide a functional system for producing nitric oxide that is derived from natural products. Previously no natural products were believed effective in generating nitric oxide activity in patients. The disclosed embodiments include a novel daily regimen that can safely and effectively restore nitric oxide levels as well as reduce blood biomarkers routinely used to assess patient risks for developing cardiovascular disease.

The disclosed embodiments are distinct from nitric oxide production through endothelial production using the L-arginine pathway. The disclosed embodiments utilize dietary sources of nitrite, nitrate and anti-oxidants. As noted, the L-arginine pathway becomes dysfunctional with age and would benefit from a back-up system to compensate. Eating a diet rich in nitric oxide activity, e.g., sufficient nitrite and nitrate along with antioxidants and botanicals to facilitate reduction to nitric oxide, aids to overcome an insufficiency in endothelial derived nitric oxide. However, ordinary diets are insufficient. The disclosed embodiments address the inherent inefficiencies that exist for reducing nitrite to nitric oxide along the physiological oxygen gradient.

There are certain rich sources of nitrate such as herbs, beet root and nitrate salts, for example, that generate supraphysiological concentrations of nitrite. Together with nitrite reductase, these components effectively reduce nitrite to nitric oxide along the physiological oxygen gradient in vivo. Utilizing nitrite as a substrate for nitric oxide production is ideal for restoring both cyclic guanosine monophosphate (cGMP) dependent and independent nitric oxide signaling.

The recognition of an enterosalivary circulation of nitrate and subsequent production of nitrite and nitric oxide reveals a system then for not only assessing nitric oxide and nitrite activity but also a means to therapeutically intervene in conditions associated with nitric oxide insufficiency.

The disclosed embodiments can be used as a means to treat, prevent or cure conditions associated with nitric oxide insufficiency. In at least one embodiment, the delivery system is a dissolvable formulation, such as a lozenge, that becomes activated and generates nitric oxide upon dissolution. The disclosed embodiments may be administered to correct and treat conditions of nitric oxide insufficiency in humans. Humans with conditions associated with nitric oxide insufficiency such as endothelial dysfunction, coronary artery disease, peripheral artery disease, diabetes, smokers, hypertension, sedentary lifestyle, any genetic condition known to affect endogenous nitric oxide production, and/or family history of cardiovascular disease can be administered the appropriate amount of formulation (for example, one or two lozenges per day) as a means to restore their nitric oxide homeostasis.

Kits of the Invention

Any of the compositions described herein may be comprised in a kit. In a non-limiting example, one or more compounds that either alone or with another compound increases nitric oxide production orally may be comprised in a kit. In specific embodiments, the kit comprises nitrite, nitrate, nitrite reductase, L-arginine, L-citrulline, a carrier, a disintegrating agent, a compactible excipient, and/or a filler; in particular embodiments one or more of these compounds are configured in a delivery system for oral production of nitric oxide. The delivery system may be an oral disintegrating tablet, as an example. The kits will comprise any of the agents in suitable container means.

Where appropriate, the components of the kits may be packaged either in aqueous media or in lyophilized form. In some embodiments, the container means of the kits will generally include at least one vial, test tube, flask, bottle, syringe or other container means, into which a component may be placed, and preferably, suitably aliquoted. Where there are more than one component in the kit, the kit also may generally contain a second, third or other additional container into which the additional components may be separately placed. However, various combinations of components may be comprised in a vial. The kits of the present invention also will typically include a means for containing the dispersible system in close confinement for commercial sale. Such containers may include injection or blow-molded plastic containers into which the compositions are retained.

In embodiments of the invention, the formulation in a dispersible system is protected by using packaging preservation, such as a unit dose blister with minimal water permeation film. In some embodiments, the present invention uses a coated or DC grade ascorbic acid to minimize surface area exposure and reaction. The delivery system in the kit is preferably packaged to resist moisture. In specific cases of the kit, the system is adapted to maintain uniform distribution of nitrite in a package.

EXAMPLES

The following examples are included to demonstrate preferred embodiments of the inventions. It should be appreciated by those of skill in the art that the techniques disclosed in the examples which follow represent techniques discovered by the inventor to function well in the practice of the inventions, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the inventions.

Example 1

Exemplary Formulations

FIG. 1A shows the nitric oxide release profile of the delivery system when dissolved in neutral buffer solution connected to a nitric oxide analyzer. The functional components were placed in a reaction vessel at 37° C. and connected to an ozone-based chemiluminescent nitric oxide analyzer. Immediately upon dissolution, nitric oxide is produced and sustained for several minutes. To demonstrate that the activity is also functional in the mouth, the sample tubing from the nitric oxide analyzer was placed in the mouth of human subject. Baseline nitric oxide levels in the breath were collected for 60 seconds. At 60 seconds, the nitric oxide formulation was placed in the mouth and nitric oxide was immediately detected. FIG. 1B shows the nitric oxide release profile when allowed to dissolve in the mouth of a human subject. Up to 12,000 ppb nitric oxide gas was detected for up to 5-6 minutes while the lozenge was dissolving. This nitric oxide is absorbed and transported throughout the body.

Figure 2:
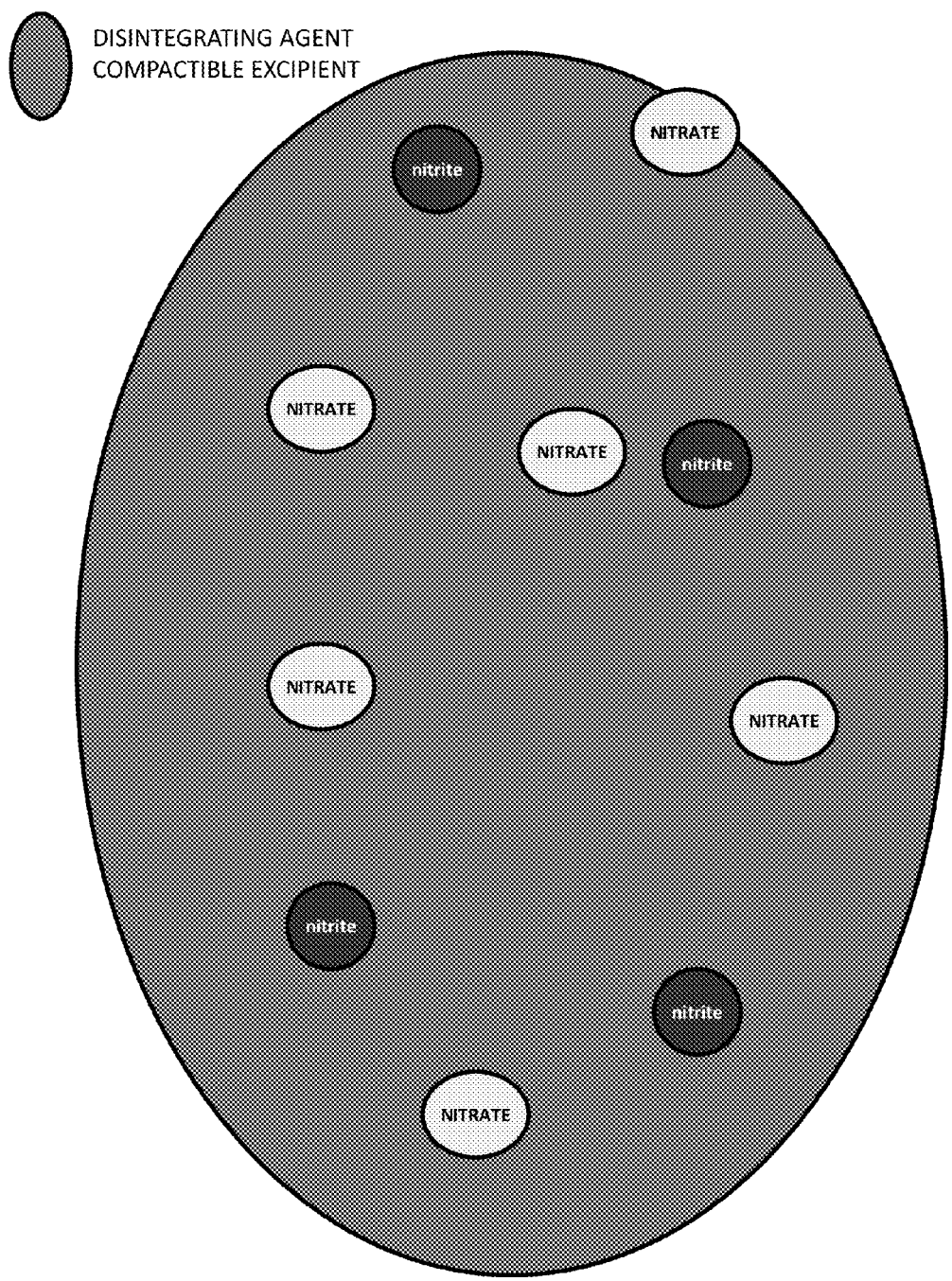
FIG. 2 shows a particular embodiment of the inventive delivery system formed of nitrite, and in some cases nitrate, disintegrating agent and compactable excipient.

FIG. 2 shows a particular embodiment of the inventive delivery system formed of a nitrite, and in some cases nitrate, disintegrating agent and compactable excipient. These components may be integrated into a single form, such as a compact or lozenge, in particular embodiments.

The active ingredients may comprise nitrite, nitrate, nitric oxide, L-arginine, L-citrulline, or a combination thereof. The active ingredients may comprise hawthorne berry, bilberry, and/or beet root. The active ingredients may comprise one or more compositions that have nitrite reductase activity. The nitrite may comprise sodium nitrite and/or potassium nitrite, for example, or any cultured vegetable extract wherein nitrate has been reduced to nitrite. The nitrate may comprise sodium nitrate and/or potassium nitrate, for example or any naturally containing nitrate food such as green leafy vegetables or beet root. The nitrite is preferably a nitrite salt. The nitrite may also be sodium nitrite, potassium nitrite, cultured vegetable extracts such as celery, beet, kale, spinach, arugula, seaweed, kelp, or any food component containing a high concentration of nitrite, preferably greater than 1% nitrite.

A nitrate source is included in alternative embodiments. The nitrate source may be in the form of beet root, sodium nitrate, potassium nitrate, vegetable extract or any other source with high nitrate concentration, preferably having greater than 1% nitrate. Examples of nitrate rich sources include beet, kale, spinach, arugala, seaweed and kelp.

L-citruline and L-arginine may also be included, as well as any modifications of thereto.

In another embodiment, the delivery system includes a nitrite and carrier for the nitrite. The nitrite is preferably from a salt, plant, natural occurring product, and/or cultured vegetable extract.

In embodiments of the invention, the composition comprises a nitrite salt (for example, sodium or potassium) wherein the nitrite salt is provided in an amount ranging from about 10 mg to about 100 mg; a nitrate salt (for example, sodium or potassium), wherein the nitrate salt is provided in an amount ranging from about 50 mg to about 500 mg; and optionally ascorbic acid, wherein the ascorbic acid is provided in an amount ranging from about 100 mg to about 2000 mg; and in some embodiments such components are provided in a single dose. In specific embodiments, the composition comprises from about 1 weight part to about 8 weight parts nitrite, from about 5 weight parts to about 50 weight parts nitrate, and from about 20 weight parts to about 200 weight parts ascorbic acid. In some cases, the active ingredients further comprise L-arginine, such as, for example, from about 20 weight parts to about 200 weight parts L-arginine.

The reductase is preferably a nitrite reductase. Nitrite reductase compounds include beet, hawthorne berry, green tea extract, pine bark, schizandra, ginkgo, rhodiola, artichoke or any other component capable of reducing nitrite to nitric oxide. The reductase component donates an electron to nitrite to generating nitric oxide when reacted with nitrite. The preferred amount of the reductase ranges from 10 mg to 10,000 mg of solid powder of the identified nitrite reductase component. An effective dose of nitrite is the range of 1 mg to 100 mg. The reductase is included is the range of 10 mg to 10,000 mg.

In certain embodiments of the invention, active component sizes include ranges from 50-300 microns. Active ingredients include at least sodium nitrite, potassium nitrite, cultured vegetable extracts such as celery, or any food component containing greater than 1% nitrite, for example. In some cases, other ingredients are employed, such as L-arginine or L-citrulline. In particular embodiments, compounds with nitrite reductase activity are employed, such as beet, hawthorne berry, green tea extract, pine bark, schizandra, ginkgo, rhodiola, artichoke or any natural product capable of reducing nitrite to nitric oxide.

A variety of types of dispensible systems may be employed in embodiments of the invention, including orally dispersible powders, powders for reconstitution, granules, bi- and multiphase delivery systems (including suspension and emulsions), multiple-layer tablet and/or wafers, for example. A skilled artisan recognizes that such types of systems may employ all type of celluloses, sugars, sugar alcohols, polyols, fibers, non-fiber bulking agent, compressible salt and carbohydrates, medium chain triglycerides, fixed oil, and/or partially hydrogenated oils, for example. To prevent the reactive components in these exemplary dispensing systems (i.e., nitrite, nitrate and reductase) from reacting prior to delivery, one may employ a system that is neutral and maintains a low moisture environment, such as having low water content (such as less than 10%) and in specific embodiments less than 6% water content. The carrier and active components are packaged so as not to react prior to consumption, such as by using minimal permeable containers and/or with dessicant. Unit dose packaging may also be employed.

The disintegrating agent may comprise Modified starches (i.e., Sodium Starch Glycol ate), Modified Cellulose (i.e., Croscarmellose Sodium), and/or cross-linked polymer, such as cross-linked poly-vinylpyrrolidone (i.e., Crospovidone). The disintegrating agent tends to absorb fluid upon contact and cause the delivery system to disintegrate and dissolve. In one embodiment, the disintegrating agent functions like sponge and facilitates retention of fluid to allow for volume expansion. The expansion breaks apart the lozenge in situ.

The disintegrating agent is preferably inert and compressible. To prevent reaction with nitrite or nitrate sources, the disintegrating agent preferably has the following properties, for example: wicking and swelling for volume expansion. Disintegrating agents may range in amount from 0.5 to 20%, and in specific embodiments range from 5-10%.

The compactable excipient may be one or more of Lactose, Dibasic Calcium Phosphate, Starch, Microcrystalline Cellulose, Sugars (Sucrose, Fructose, Dextrose), Sugar Alcohols, and/or Celluloses (Hydroxy and Methyl). The compactable excipient is adapted to be compressed with the other components of the delivery system and maintain the delivery system in a compressed form. The compactible excipient maintains the disintegrating agent and other components are together in non-reactive contact within the delivery system. The compactable excipient is preferably chemically inert so as not to react with the nitrite, nitrate, disintegrating agent, or any additional components. The compactable excipient does not absorb fluid and may be hydrophobic to mitigate reaction in the delivery system. The compactable excipient may be non-hydroscopic and positioned in the delivery system so as to protect water sensitive actives. The compactible excipient preferably has a narrow particle size distribution so that no segregation occurs and an uniform mixture of the ingredients is provided. Compactable excipient amounts may range from 10-90%, and in specific embodiments range from 50-75%.

Upon administration, the delivery system reacts with fluids in the body and begins to dissolve. The nitrite, disintegrating agent, compactable excipient and other components (if appropriate) maintain their compressed form until they react with fluid in the body, such as saliva from the buccal cavity of an animal. Fluid causes the disintegrating agent to expand which causes the compactable excipient and other components to break apart upon expansion. As the delivery system to breaks apart the reactive components come into surface contact with each other and bacteria existing in-vivo, such as in the crypts of the human tongue. This embodiment may also include reductase for promoting the reduction of nitrite or nitrate sources to nitric oxide.

Figure 3:
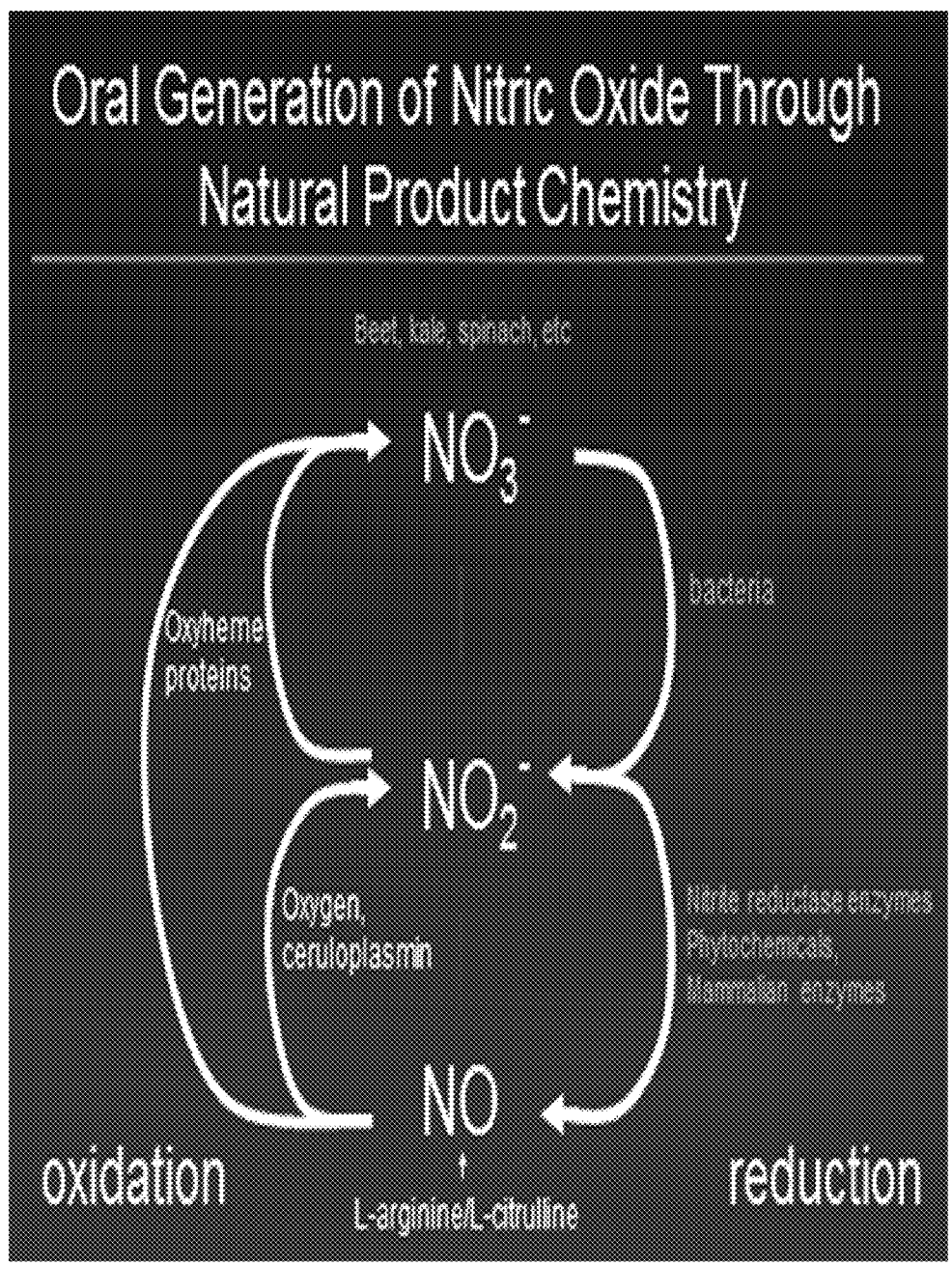
FIG. 3 illustrates oral generation of nitric oxide through natural product chemistry.

FIG. 3 illustrates the chemistry that proceeds upon administration of the delivery system.

The dispersable medium may be made from one or more sugars, dispersing agents, flavors, sweetener, color, alcohols, maltodextren, or other organic fillers such as cellulosis or inorganic fillers such as phosphate salt. The dispersible medium physically separates the nitrite, reductase and other reactive components so that they to come in contact with each other and react in vivo to generate nitric oxide in situ. The system is dispersable, which in at least some embodiments means a uniform mixture is created upon reconstitution to allow ingredient to interact appropriately upon dosing.

In certain embodiments of the invention, a filler is employed to hold the disintegrating agents and compactible excipients together in the delivery system (including lozenges); fillers with binding properties may be employed, therefore, including starch, sugar, sugar alcohol, or one or more celluloses, for example. Fillers may be present in the composition in a range from 1-99%, and in specific embodiments it is from 60-90%.

Embodiments of the delivery system may be a liquid, powder, solid (dissolvable in oral cavity), semi-solid (cream, gel, emulsion, suspension) heterogenic liquid (multi-phase), film, topical, suppository, biofilms, or any another medium that tends to maintain the nitrite and reductase in a non-reactive relationship within a package. A barrier is optionally included in the delivery system so as to prevent contact of the nitrite and reductase with each other and to minimize exposure of the surface of reactive components.

Figure 4A:
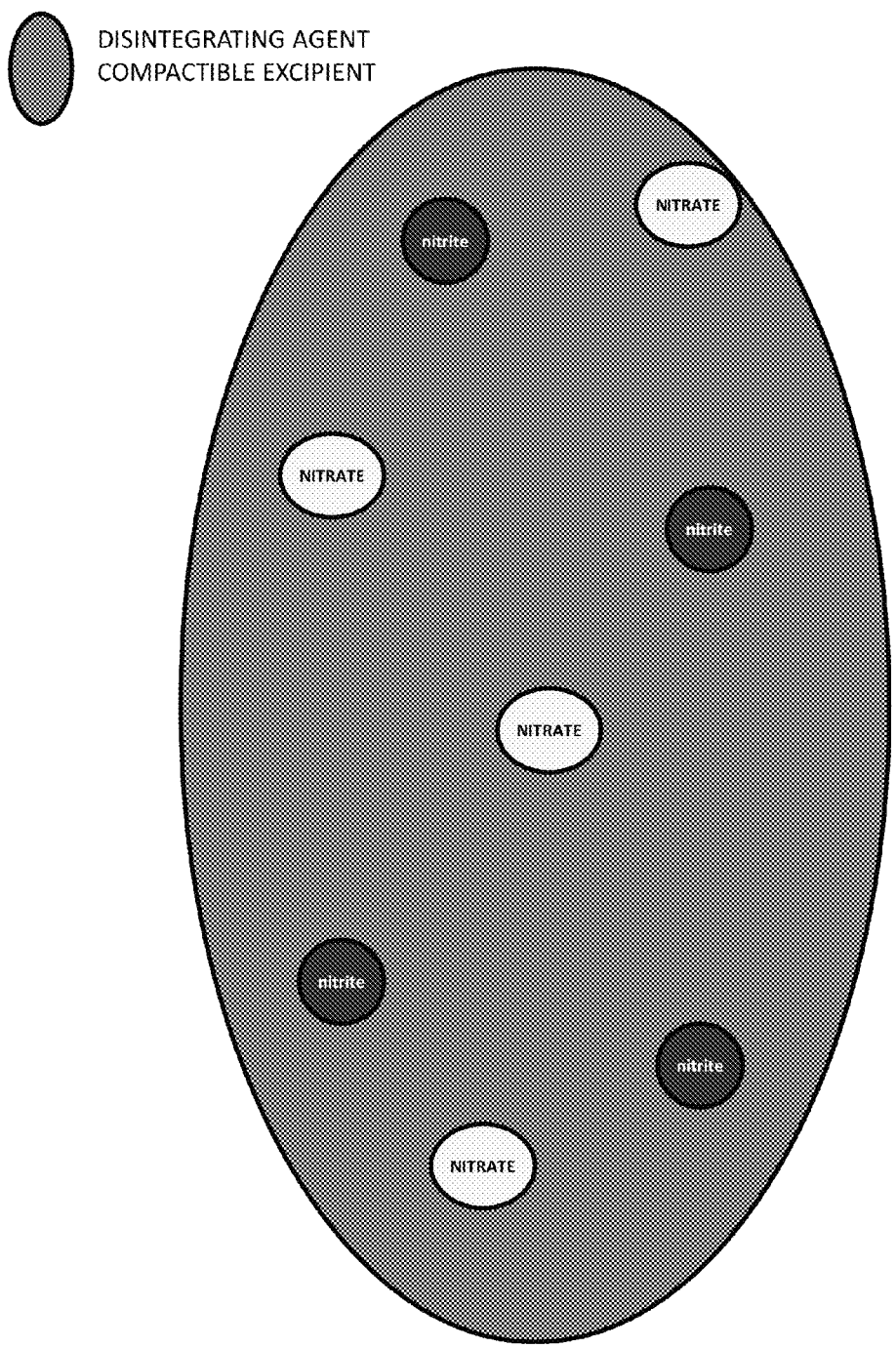
FIGS. 4A and 4B provide an exemplary illustration of a delivery system that encompasses a barrier in the formulation to separate particular components.
Figure 4B:
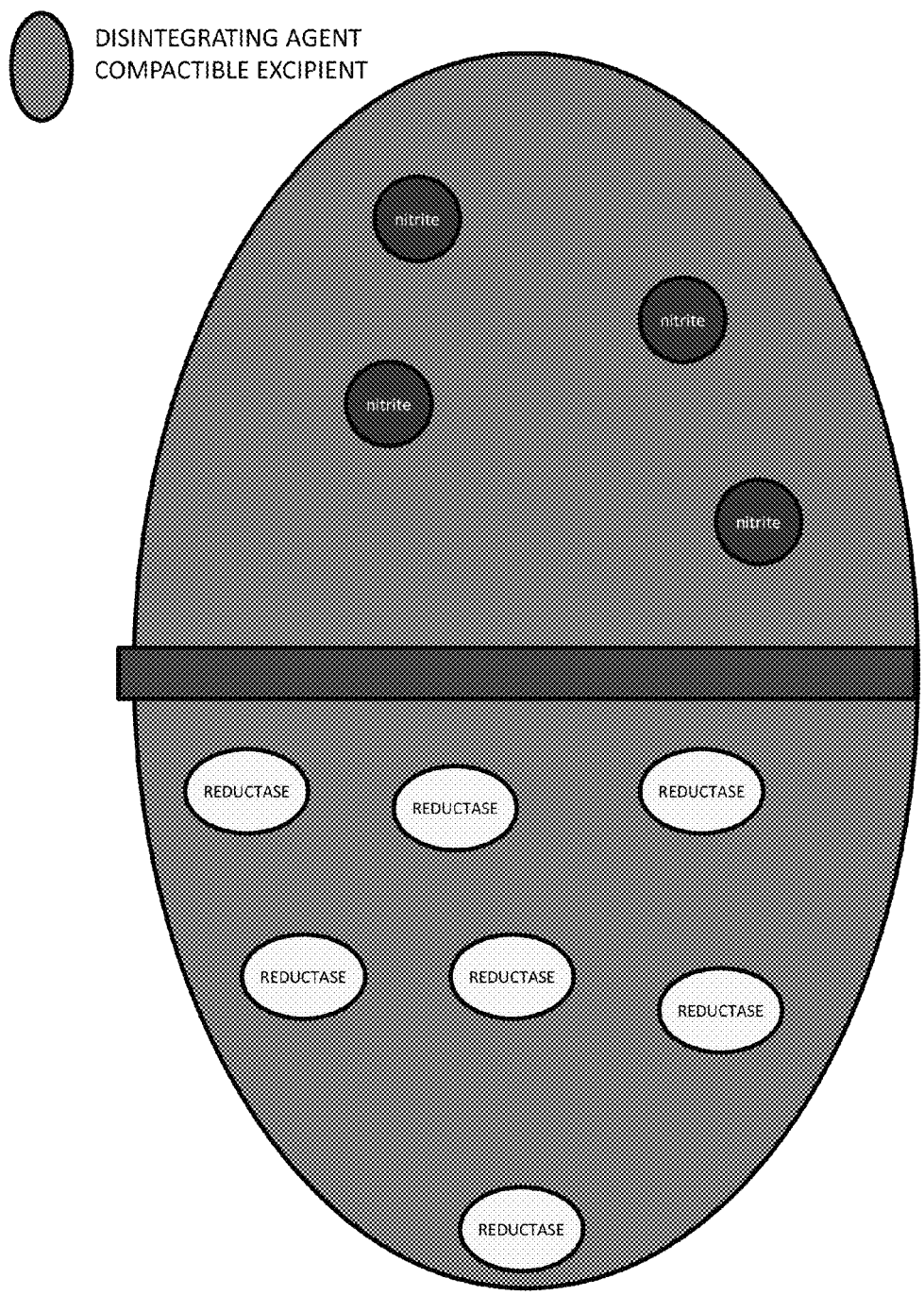
Figure 5:
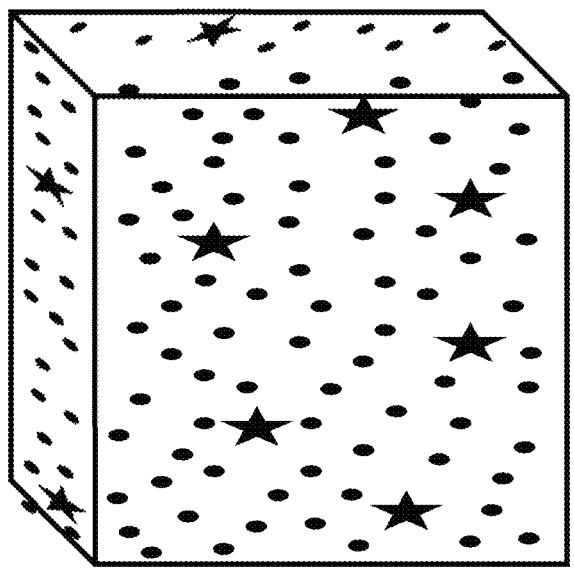
FIG. 5 illustrates an exemplary embodiment of the delivery system.

FIGS. 4A and 4B show exemplary delivery systems formed of nitrite, nitrate, and/or reductase, and one or more dispensable excipients. In FIG. 4A the barrier is greater concentration of inert particles than active particles. In FIG. 4B, the barrier is a layer of inert material between active ingredients on the tablet. The barrier is preferably formed of a sugar, dispersing agent, flavors, sweetener, color, alcohols, maltodextren, or other fillers to provide separation between the nitrite and reductase. The barrier breaks down in vivo upon contact with fluid so that the nitrite and reductase to come in contact, react, and thus generate nitric oxide. The chemical reaction of FIG. 3 then occurs FIG. 5 shows an exemplary delivery system including a carrier. The carrier provides for administration (i.e., delivery) of nitrite to buccal cavity. The inert components are present in such an excess over the reactive components (nitrate, nitrite, and/or reductase) that the reactive components cannot reach with each other. In particular embodiments, the percentage of inert components is greater than the percentage of reactive components. In some embodiments, there are enough inert components to prevent reaction of the reactive components.

The carrier may be in the form of Diluents/Fillers (such as from 1-99%, including from 60-90%) or coating systems (such as from 0.1-20%, including from 0.1-10%)(composition of sugars, sugar alcohols, celluloses, acrylates, waxes and fats), in certain embodiments. The carrier is adapted to maintain uniform distribution of said nitrite in a package (and during administration). The carrier is inert so that it does not react with active components. The carrier does not react with the nitrite. It is inert, both in the package and during administration. Nor does the carrier impede the reaction of nitrite with other components. Nor does it impede the absorption of nitrite in said buccal cavity. The carrier does not tend to swell upon contact with a fluid (i.e., is non-hydroscopic). The carrier may be digestive or non-digestive. The carrier may be organic or inorganic. T The carrier allows for an efficacious dose to be delivered (e.g., at least 75%, 80%, 85%, 90%, 95%, or more), in at least certain embodiments. The carrier preferably has less than or equal to 50% particle size difference from the nitrite. The carrier preferably has a particle size ranging from 50 to 500 microns, including from 100-350 microns.

In embodiments of the invention, there is not a carrier but rather an excipient separator or a physical separator, which prevent two or more reactive or incompatible ingredients from reacting while in the dosage form but allow them to become active in vivo or once dosification takes place.

Embodiments of the disintegrating agents in the formula have the ability to draw water into the porous network of the tablet, which allows for the disintegration to occur. The mechanism of action can be a combination of water wicking and swelling. Water wicking mainly refers to the ability to draw water into the tablet. After the necessary water penetration, swelling or volume expansion immediately occurs allowing all of the component to be released. Water wicking does not necessarily mean a volume increase. The swelling overcomes the forces that allowed the tablet compaction to occur, in particular embodiments.

The properties (physical or chemical) of the disintegrating agent, compactible excipients, or other components in the delivery system that prevent the nitrite, nitrate and reductase from reacting in the lozenge are that they are mainly an inert, non-reactive material that by dilution or coating allows the reactive components to be physically separated until ingestion or dosing.

Additional components may include reductase for the nitrite, ascorbic acid, and polyphenols. Ascorbic acid includes magnesium ascorbate, sodium ascorbate, calcium ascorbate, potassium ascorbate, zinc ascorbate, molybdenum ascorbate, chromium ascorbate, manganese ascorbate or any other mineral ascorbate. Polyphenols include flavonoids, stilbenoids, tannins, gallic acid or any other polyphenol. Polyphenols may be in the form of a powder, extract, or liquid. The polyphenol has the following effect in that it can reduce nitrite to NO. This in beneficial because the interaction of nitrite with polyphenols can generate NO while inhibiting nitrosation reactions. The preferred range of the polyphenols is 10-10,000 mg.

In embodiments of the invention, there is a formulation that has certain components in particular ratios that generate a synergistic effect in carrying out the goal of the present embodiments. The ratio of particular significance is nitrite:ascorbic acid. In the preferred embodiment, the range is at least 1:1.5 in order to prevent nitrosative chemistry and facilitate reduction to nitric oxide. In one embodiment, the ratio is 1:1.5-4.9. In another embodiment, the ratio is 1:1.5-5.0. In another embodiment, the ratio is 1:1.5-10.0. In some embodiments, the range of nitrite:nitrate:ascorbic acid:nitrite reductase is 1:1-100:1.5-10:1-100, or 1:0.1-1.0:0.001-0.5:0.05-0.99, for example.

In another embodiment the delivery system includes nitrite, nitrite reductase, ascorbic acid, and polyphenols. A disintegrating agent and a compactable excipient may also be included.

Figure 6A:
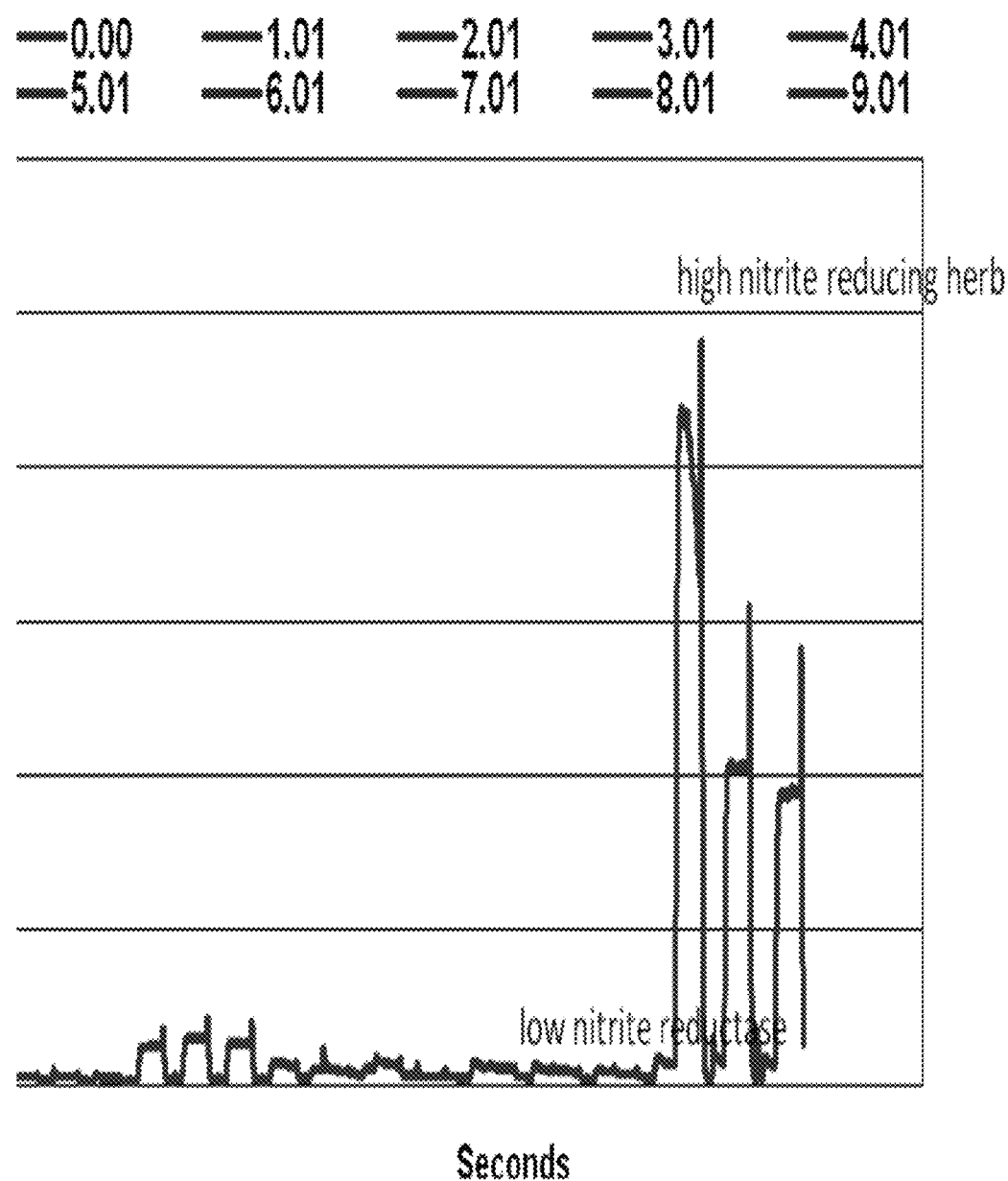
FIG. 6A shows in vitro test data of the nitric release profile produced by the delivery system.

FIG. 6A shows in vitro test data of the nitric release profile produced by the delivery system. The nitrite reductase activity was detected by ozone based gas phase chemiluminescent detection of nitric oxide gas or through a nitric oxide sensor. Any natural product that is capable of generating NO gas when nitrite is added is classified as a nitrite reductase.

Figure 6B:
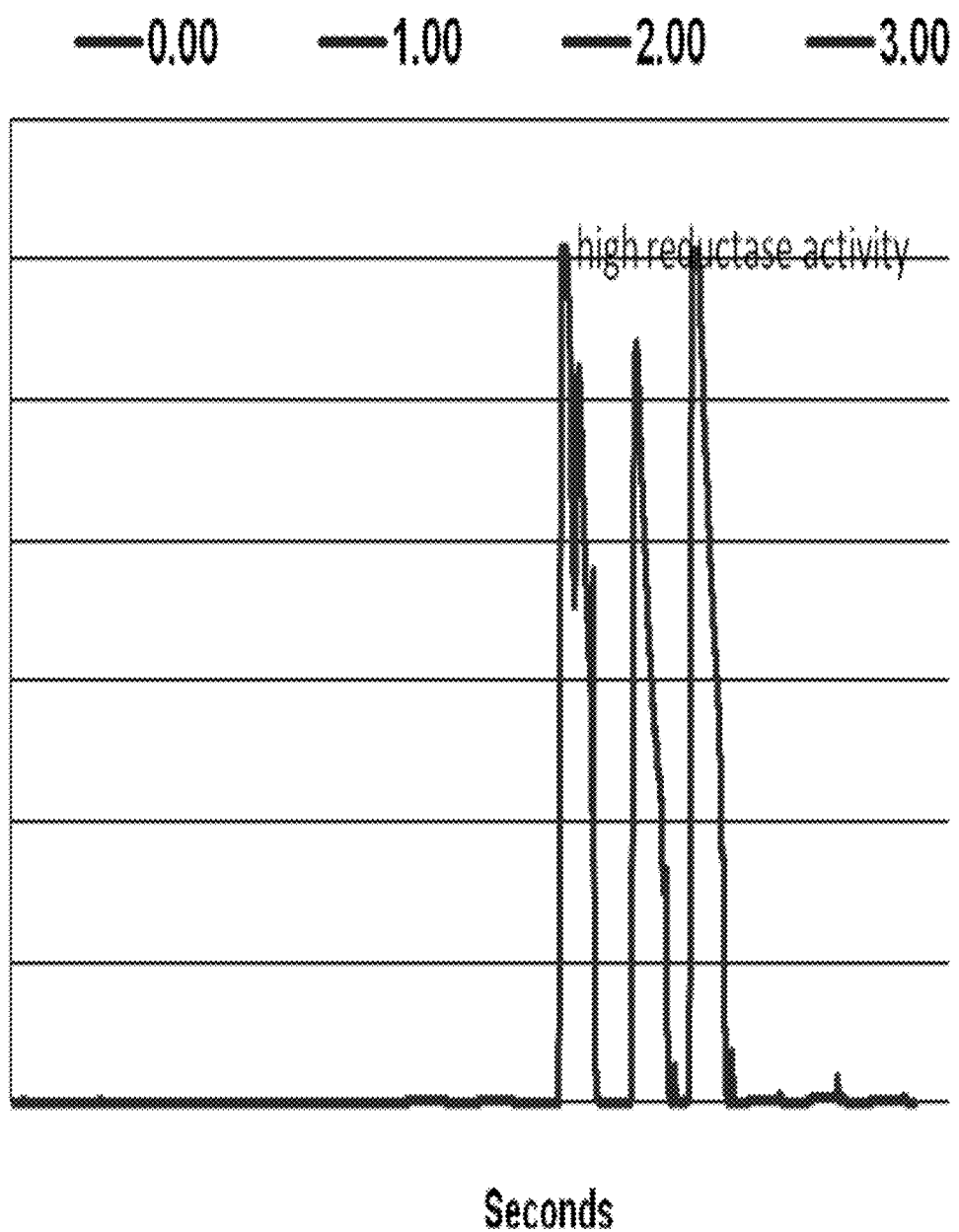
FIG. 6B shows the reductase activity tested from a tablet with the 10 mg nitrite formulation.

FIG. 6B shows the reductase activity tested from a tablet with the 10 mg nitrite formulation.

Figure 7:
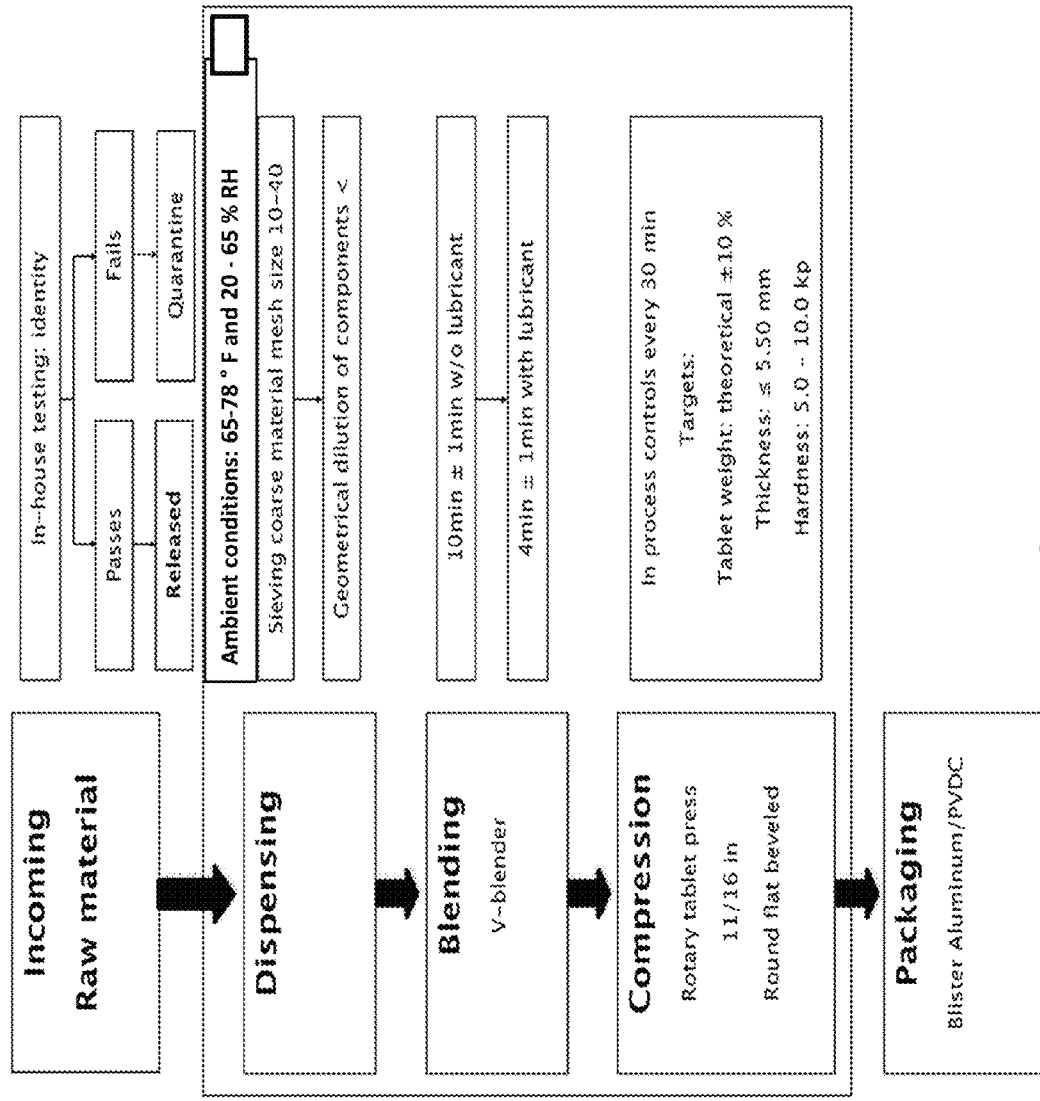
FIG. 7 illustrates an exemplary manufacturing method to generated a composition embodiment.

One embodiment of the present invention is manufactured by dispensing the ingredients at ambient conditions in a temperature and humidity range of 65-78° F. and 20-65% RH, respectively. Raw materials are passed through sieves mesh size 10-40. Compounds with contents lower than 0.7% w/w (except silicon dioxide) are geometrically diluted before adding to the total blend by blending with equal amounts of diluents in a properly sized V-blender for 5 minutes and further blending with doubled amount of diluents for another 5 minutes. The dispensed ingredients are then blended in a properly sized V-blender at ambient conditions in a temperature and humidity range of 65-78° F. and 20-65% RH, respectively. All ingredients except lubricants are blended for 10 minutes±1 minutes. Lubricants are then added and blended for another 4 minutes±1 minutes (see FIG. 7).

Compression of the blend is performed on a rotary tablet press equipped with size 11/16 in round flat bevel shaped punches at ambient conditions in a temperature and humidity range of 65-78 ° F. and 20-65% RH, respectively. Process controls are carried out to ensure the production of tablets with a thickness of NMT 5.5 mm and hardness in the range of 5.0-10.0 kp, fulfilling the requirements of uniformity of mass of the United States Pharmacopoeia.

One embodiment includes the following components:

| Ingredients | Mg | Weight Distribution (%) |
|---|---|---|
| Active Ingredients: | 521.00 | 36.82 |
| Other Ingredients: | | |
| Mannitol | 740.00 | 52.29 |
| Modified Cellulose | 45.00 | 3.18 |
| Natural Orange Flavor | 23.00 | 1.63 |
| Stevia | 6.00 | 0.42 |
| Xylitol | 51.00 | 3.60 |
| Magnesium Stearate | 16.50 | 1.17 |
| Silicon Dioxide | 3.60 | 0.25 |
| Carmine | 9.00 | 0.64 |
| Total | 1414.10 | 100.00 |

| Ingredients | Mg |
|---|---|
| Active Ingredients: | 521.00 |
| 1) Vitamin C | 100.00 |
| 2) Vitamin B12 | 1.00 |
| 3) Nitric Oxide Producing Components | 420.00 |
| a) Beet Root | 200 |
| b) Hawthorn | 100 |
| c) L-Citrulline | 100 |
| d) Sodium Nitrite | 20 |

One exemplary embodiment of the formulation is as follows:
1-150 mg sodium nitrite
5-500 mg Vitamin C
50-500 mg Beetroot
10-500 mg Hawthorn
Vitamin B12 1-1000 □g Filler, sugars, disintegrants, natural flavor and colors may also be included in the formulation. After blending, this mixture is blended compressed and packaged in moisture protective containers in blistered package using aluminum foil and polyvinylidenechloride (PVDC) films that offer an exceptional barrier properties against moisture and oxygen penetration PVDC film into six tablet count blisters.

Although embodiments of the present invention and its advantages have been described in detail, it should be understood that various changes, substitutions and alterations can be made herein without departing from the spirit and scope of the inventions as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present inventions. Accordingly, the appended claims are intended to include within their scope such processes, machines, manufacture, compositions of matter, means, methods, or steps.

What is claimed is:

1. A method of increasing levels of nitric oxide in an individual, comprising the step of orally delivering a therapeutically effective amount of a composition to the individual, wherein the composition comprises:
   at least one nitric oxide-producing component; and
   a dispersible medium adapted to be consumed in the oral cavity;
   wherein the nitric oxide-producing component is adapted to generate nitric oxide in vivo upon consumption of the dispersible medium, and wherein the composition comprises about 1 mg to about 150 mg of a nitrite salt and about 10 mg to about 10,000 mg of nitrite reductase and wherein the composition comprises about 1,000 mg to about 10,000 mg of beet root in powder form.

2. The method of claim 1, wherein the composition comprises about 10 mg to 500 mg of nitrate.

3. A method of enhancing cardiovascular performance in an individual, comprising the step of orally administering a composition to the individual, wherein the composition comprises:
   at least one nitric oxide-producing component; and
   a dispersible medium adapted to be consumed in the oral cavity;
   wherein the nitric oxide-producing component is adapted to generate nitric oxide in vivo upon consumption of the dispersible medium, and wherein the composition comprises about 1 mg to about 150 mg of a nitrite salt and about 10 mg to about 10,000 mg of nitrite reductase and wherein the composition comprises about 1,000 mg to about 10,000 mg of beet root in powder form.

4. The method of claim 3, wherein the composition comprises about 10 mg to 500 mg of nitrate.

* * * * *